Dec. 4, 1962 D. H. MOREY, JR Plant Pat. 2,199
ROSE PLANT
Filed Jan. 29, 1962
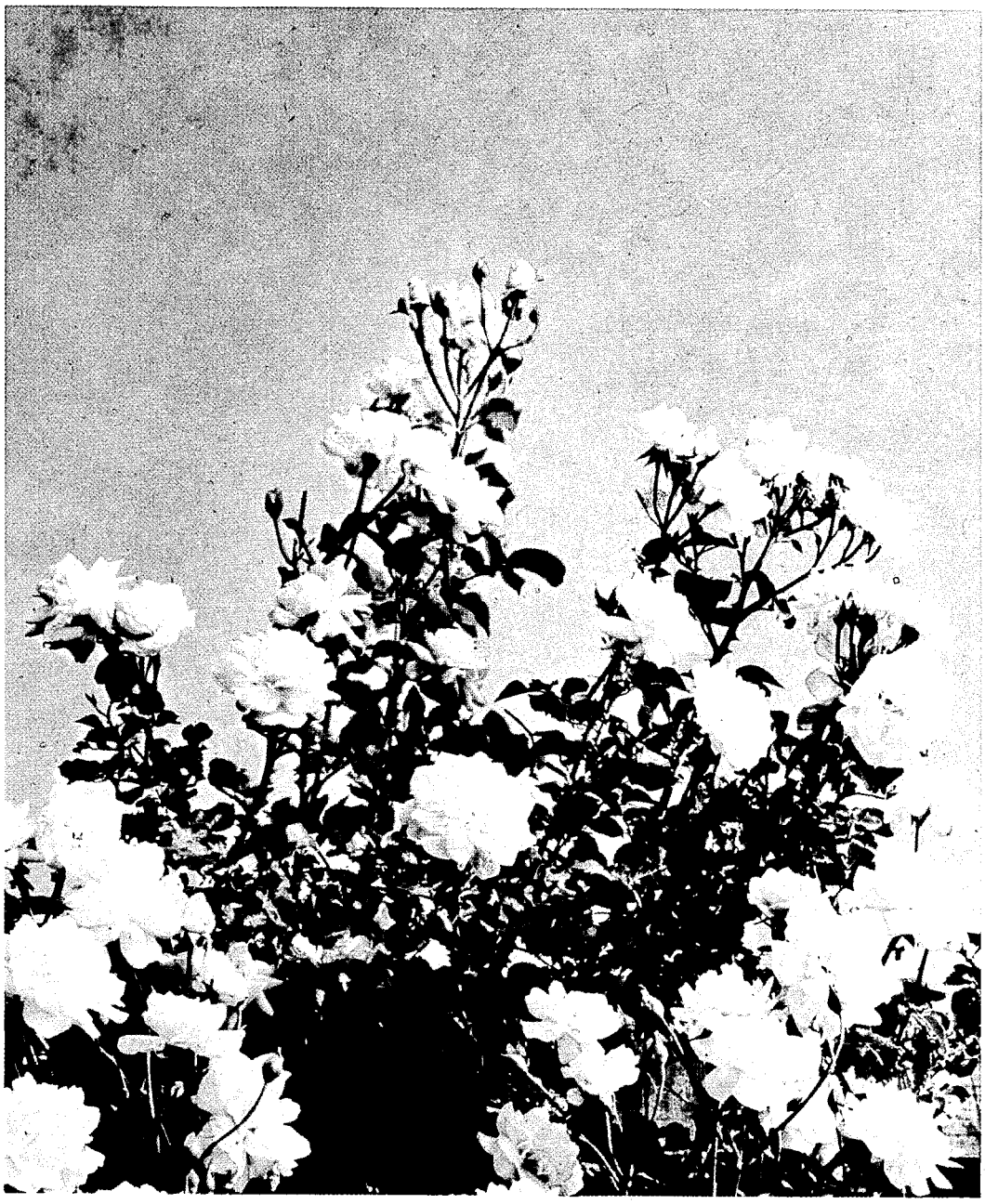
Inventor.
Dennison H. Morey, Jr.
By: Robb & Robb
Attorneys.

United States Patent Office

Plant Pat. 2,199
Patented Dec. 4, 1962

2,199
ROSE PLANT

Dennison H. Morey, Jr., Pleasanton, Calif., assignor to Jackson & Perkins Company, Newark, N.Y., a corporation of New York Filed Jan. 29, 1962, Ser. No. 169,693
1 Claim. (Cl. 47—61)

The present invention relates to a new and distinct variety of rose plant of the climber class, which was originated by me by crossing an unnamed and unpatented seedling derived from a cross of "Captain Thomas" (Plant Patent No. 393) × "Joanna Hill" (unpatented) with the variety "Lydia" (unpatented).

The primary objective of this breeding was to produce a new rose variety of the climber class having good vigor and hardiness, combined with flowers of non-fading yellow color. This objective was fully achieved, along with other desirable features which represent a unique combination in rose plants of the climber class, as evidenced by the following characteristics which are outstanding in the new variety, and which distinguish it from its parents, as well as from all other varieties of which I am aware:

(1) Vigorous and hardy habits of growth;
(2) Free-flowering and remontant blooming habits;
(3) Large flower size, with the flowers borne both singly and in clusters; and
(4) A distinctive, attractive and non-fading yellow general color tonality of the flowers corresponding to Martius Yellow, lightly overcast with Empire Yellow.

Asexual reproduction of my new variety by budding, as performed at Pleasanton, California, and also at Newark, New York, shows that the foregoing characteristics and distinctions come true to form and are established and transmitted through succeeding propagations.

The accompanying drawing shows typical specimens of the vegetative growth and flowers of my new variety in different stages of development and as depicted partly in color and partly in black and white.

The following is a detailed description of my new variety, with color terminology in accordance with Ridgway's Color Standards and Nomenclature:

Parentage: Seedling.
*Seed parent.*—An unnamed seedling derived from a cross of "Captain Thomas" × "Joanna Hill."
*Pollen parent.*—"Lydia."
Classification:
*Botanic.*—Climber.
*Commercial.*—Climber.

*Flower*

(Observations made from specimens grown outdoors at Newark, New York, during the early morning in the latter part of the month of August.)
Blooming habit: Recurrent—intermittent; free-flowering.
Bud:
*Size.*—Medium.
*Form.*—Ovoid; is not affected by wet or hot weather.
*Color.*—When sepals first divide—Pale Greenish Yellow, Plate 5; when petals begin to unfurl—Empire Yellow, Plate 4, with upper half of petals lightly overcast with Pinard Yellow, Plate 4; when half-blown—inside of petals—Lemon Chrome, Plate 4, with upper half of petals lightly overcast with Baryta Yellow, Plate 4; reverse of petals—Pinard Yellow, Plate 4, with lower half of petals lightly overcast with Empire Yellow, Plate 4.
*Sepals.*—Slightly branched; curl back when petals begin to unfurl. Color—inside—Light Fluorite Green, Plate 32; outside—Biscay Green, Plate 17.

*Calyx.*—Color—Biscay Green, Plate 17. Shape—funnel. Size—small. Aspect—smooth. Odor when rubbed—none.
*Peduncle.*—Length — medium. Aspect — rough. Strength—erect; slender. Color—Lettuce Green, Plate 5.
*Opening.*—Opens up well; is not affected by adverse weather conditions.
Bloom:
*Size.*—Large. Average size when fully expanded—from 4½ inches to 5¼ inches.
*Borne.*—Both singly and in clusters.
*Stems.*—Medium length; normal strength.
*Form (when first open).*—Cupped. Permanence—retains its form to the end.
*Petalage.*—Double (full but open center). Number of petals under normal conditions—from 25 to 30.
*Color.*—Center of flower—Empire Yellow, Plate 4, lightly overcast with Martius Yellow, Plate 4. Outer petals—Sulphur Yellow, Plate 5, with lower half of petals lightly overcast with Pale Lemon Yellow, Plate 4. Base of petals (aiglet)—Lemon Chrome, Plate 4. Inside of petals—Martius Yellow, Plate 4, lightly overcast with Empire Yellow, Plate 4. Reverse of petals—Sulphur Yellow, Plate 5. General tonality from a distance—Martius Yellow, Plate 4, lightly overcast with Empire Yellow, Plate 4.
*Discoloration.*—General tonality at end of first day—Martius Yellow, Plate 4, lightly overcast with Empire Yellow, Plate 4. Second day—Martius Yellow, Plate 4, lightly overcast with Empire Yellow, Plate 4. Third day—Sulphur Yellow, Plate 5, with lower half of petals lightly overcast with Pale Lemon Yellow, Plate 4.
Petals:
*Texture.*—Leathery; is not affected by wet or hot weather.
*Appearance.*—Inside—satiny. Outside—shiny.
*Form.*—Oval.
*Arrangement.*—Imbricated (regularly arranged shingle-like).
*Petaloids in center.*—Few; large.
*Persistence.*—Drop off cleanly.
*Fragrance.* — Moderate. Nature fruity (Russet apple).
*Lasting quality.*—On the plant—long. As cut flower—long.

*Genital Organs*

Stamens, anthers: Medium size; many; regularly arranged around styles. Color—Warm Buff, Plate 15.
Stamens, filaments (threads): Medium length. Color—Flesh Pink, Plate 13.
Pollen: Color—Light Buff, Plate 15.
Styles: Bunched; uneven length; medium length; thin.
Stigmas: Color—Pale Yellow-Orange, Plate 3.
Ovaries: All enclosed in calyx.
Hips: None.
Seeds: None.

*Plant*

Form: Climber.
Growth: Vigorous; upright; hardy.
Foliage: Compound of 5–7 leaflets.
*Size.*—Large.
*Quantity.*—Normal.
*Color.*—New foliage: Upper side—Lettuce Green, Plate 5; under side—Cosse Green, Plate 5. Old foliage: Upper side—Cress Green, Plate 31; under side—Light Cress Green, Plate 31.
*Shape.*—Oval.

*Texture.*—Upper side—leathery. Under side—smooth.

*Ribs and veins.*—Ordinary.

*Edge.*—Serrated (saw-toothed).

*Serration.*—Single; small.

*Leaf stem.*—Color—Biscay Green, Plate 17. Under side—Prickly.

*Stipules.*—Long; slightly bearded.

Wood:

*New wood.*—Color—Cosse Green, Plate 5. Bark—smooth.

*Old wood.*—Color—Bice Green, Plate 17. Bark—smooth.

Thorns:

*Thorns.*—Quantity: On main stalks from base—ordinary; on laterals from stalk—ordinary. Form—narrow base; medium length; hooked downward.

Color (when young)—Eugenia Red, Plate 13. Position—irregular.

*Prickles.*—Quantity: On main stalks—none. On laterals—none.

*Short needles.*—Quantity: On main stalks—none. On laterals—none.

I claim:

A new and distinct variety of rose plant of the climber class, substantially as herein shown and described, characterized particularly as to novelty by the unique combination of vigorous and hardy habits of growth, free-flowering and remontant blooming habits, large flower size, with the flowers borne both singly and in clusters, and a distinctive, attractive and non-fading yellow general color tonality of the flowers corresponding to Martius Yellow, lightly overcast with Empire Yellow.

No references cited.